United States Patent [19]
Harhen

[11] Patent Number: 5,692,729
[45] Date of Patent: Dec. 2, 1997

[54] PRESSURE EQUALIZED FLOW CONTROL APPARATUS AND METHOD FOR ENDOSCOPE CHANNELS

[75] Inventor: Edward Paul Harhen, Duxbury, Miss.

[73] Assignee: Vision-Sciences, Inc., Natick, Mass.

[21] Appl. No.: 602,622

[22] Filed: Feb. 16, 1996

[51] Int. Cl.$^6$ ....................................... F16K 7/04
[52] U.S. Cl. ........................ 251/4; 251/9; 604/34
[58] Field of Search .................. 251/4, 9; 138/26; 604/34

[56] References Cited

U.S. PATENT DOCUMENTS

| | | | |
|---|---|---|---|
| 2,706,101 | 4/1955 | Cantor | 251/4 |
| 3,165,123 | 1/1965 | Hawkins | 138/26 X |
| 4,852,551 | 8/1989 | Opie et al. | 128/4 |

*Primary Examiner*—John Fox
*Attorney, Agent, or Firm*—Seed and Berry LLP

[57] ABSTRACT

A pressure equalized flow control apparatus and method controls the flow of fluid through a resilient tube. The resilient tube is surrounded by an enclosed chamber having inlet and outlet ports in fluid communication with the interior of the resilient tube. A vent connecting the interior of the resilient tube with the interior of the enclosed chamber equalizes the fluid pressure inside the resilient tube with the fluid pressure outside the resilient tube within the enclosed chamber. By equalizing the pressures inside and outside of the resilient tube, the vent prevents the resilient tube from collapsing when the resilient tube is under suction. Similarly, the pressure equalization prevents a positive fluid pressure from exerting an outward force on the wall of the tube which must be overcome to pinch the tube. Thus, by using pressure equalization, the vent enables the resilient tube to have a relatively thin wall that is easily pinched to close the resilient tube.

25 Claims, 4 Drawing Sheets

PRESSURE EQUALIZED FLOW CONTROL APPARATUS AND METHOD FOR ENDOSCOPE CHANNELS

TECHNICAL FIELD

The present invention relates to fluid flow control, and more particularly, to the control of fluid flow through a thin-walled, flexible tube.

BACKGROUND OF THE INVENTION

In countless situations the flow of fluid through a tube needs to be controlled. Typically, the fluid flow control employs a valving apparatus that controls the fluid flow through the tube by altering its cross-sectional area in a localized portion of the tube.

One apparatus that relies on the control of fluid flow through a tube is a medical endoscope. Instruments to examine the rectum and sigmoid colon, known as "flexible sigmoidoscopes," are good examples of the usefulness of endoscopic technology. These devices are expensive, and they are used in a contaminated environment for a procedure which is brief (five to ten minutes) and where problems of cleaning time and contamination are important factors. There has been a large increase in the use of the flexible sigmoidoscope for use in screening symptomatic and asymptomatic patients for colon and rectal cancer. Ideally, flexible sigmoidoscopes must be used rapidly and inexpensively in order to maintain the cost of such screening at acceptable levels. Typically, a clinic would like to perform five sigmoidoscope examinations each hour. A significant problem with making such examinations quick and inexpensive is the time necessary for adequately cleaning the device.

Although endoscopes can be cleaned in about two to four minutes, this relatively cursory cleaning may not be adequate for complete disinfection or sterilization. Even a more complete cleaning, requiring on the order of eight to ten minutes, may not allow adequate cleaning, particularly in view of the increasing problems with contagious viruses. Even with the use of chemicals such as gluteraldehyde, adequate cleanliness may not be possible.

The cleaning problem not only includes the outside of the endoscope but also the multiple small channels inside the endoscope. This includes channels for air insufflation, water to wash the tip, biopsy, and suction. Each channel employs a control valve. These channels extend along the length of the endoscope and come into contact with body tissues and fluids. It is extremely difficult to adequately clean these channels even when skilled health practitioners spend a great deal of time on the cleaning procedure.

Even if endoscopes can be adequately cleaned in eight to ten minutes, the cleaning still prevents endoscopy examinations from being relatively inexpensive. While a physician may spend five to ten minutes performing some types of endoscopy, he or she will generally waste a great deal of time waiting for the endoscope to be cleaned before he or she can conduct another endoscopy. A partial solution to the "idle time" problem is to purchase multiple instruments so one can be used as the others are being cleaned. However, the expense of having duplicate endoscopes of each of the many types described above makes this solution impractical, especially for physicians' offices and smaller clinics.

As a result of these many problems, conventional endoscope cleaning techniques greatly increase the cost of endoscopic procedures. Furthermore, while the risk of contamination using endoscopes is often far less than the risk of alternative procedures, such as surgery, there is nevertheless a risk that endoscopes are not cleaned adequately to prevent the risk of transmission of infectious diseases from one patient to the next.

One approach to the problem of endoscope contamination is described in U.S. Pat. No. 4,646,722 (the '722 patent) which is incorporated herein by reference. This approach of the '722 patent involves the use of an endoscope sheath having a flexible tube surrounding the elongated core of an endoscope. The flexible tube has a transparent window near its distal end positioned in front of the viewing window of the endoscope. Channels that come into contact with the patient or the patient's body fluids (e.g., channels for taking biopsies, injecting air or injecting water to wash the window of the sheath) extend along the endoscope, either inside or outside the sheath.

After use of the endoscope, the sheath and channels are removed and disposed of, leaving the endoscope free of contamination resulting from the endoscopic procedure. An essential aspect of this approach is incorporating the channels into the system so that the flow of air or liquids through the channels can be controlled without spreading contamination. These channels are essential for many types of endoscopy. In gastroenterology, the channels are used for insufflation of air to open the otherwise closed lumen of the intestinal organs, for spraying water over the tip lens to clean off obscuring mucus, stool or blood, and for suctioning fluid, blood or mucus which is obscuring the examination. The suction channel is the same channel used in most designs for passage of a variety of instruments for diagnosis (biopsy forceps, brushes for cytology, etc.) and therapy (snares to remove polyps, probes to stop ulcer bleeding, etc.).

All of the above-described channels are contaminated in the course of an endoscopy. In the currently used endoscopes (fiberoptic and video), these channels and their valves are the most difficult portions of the endoscope to clean. The suction channel is grossly contaminated with secretions including blood, mucus and stool in every case. A valve in continuity with the inside of the channel is also instantly contaminated. The air and water channels present slightly different problems. The direction of the flow of the air and water is towards the end of the endoscope. Therefore, one might think that these channels could not become contaminated. In fact, however, because of capillary action as well as gravity, both of these small channels are always contaminated with secretions during endoscopy, including blood, stool and mucus. Further, the small size of these channels makes them very hard to clean. If any residue remains, the residue can react with gluteraldehyde, which is commonly used to clean the channels, to produce a thick substance that can plug the channel. This plug is very difficult to remove and sometimes requires that the endoscope be returned to the manufacturer for replacement of the channel. Each of the channels (air and water) also has a valve control which is in continuity with the channel and is potentially contaminated during endoscopy.

The disposable endoscope sheath described in the '722 patent reduces the contamination caused by these channels and their valves. With this protective sheath, the air, water and suction channels are entirely disposable. However, it is essential to be able to control flow through these channels to be able to perform endoscopy. Therefore, it is necessary to be able to control the flow of air or liquid through these channels yet be able to dispose of all contaminated components after the procedure. It is therefore important that the valve mechanism controlling the flow of air or liquid through the channels be simple and inexpensive so that the valve mechanism can be disposed along with the channels.

One valve system proposed to overcome disadvantages of prior an valves is disclosed in U.S. Pat. No. 4,852,551 (the '551 patent), which is assigned to the assignee of the present invention. The valve system disclosed in the '551 patent employs electrical switches located in the endoscope control body to control a remote solenoid valve that pinches a relatively thick-walled rubber tube connected to a suction source. Typically, such a rubber tube needs to have a wall thickness adequate to resist collapse and strong enough to reopen after the pinching force from the solenoid valve is released. The wall thickness will depend on the rigidity of the material used to make the tube and the strength of the suction source, but typically the wall thickness will not be less than 0.030 inches. A thinner-walled tube may be used if the tube is coupled to a source of pressurized fluid rather than to a suction source because the tube need not overcome the collapsing force of the suction. However, a thin walled tube connected to a pressure source creates the problem which the present invention is intended to solve, specifically, while a thin walled tube is relatively easy to pinch closed, it is more difficult to pinch after it has been connected to a source of pressurized fluid since the outward force exerted on the wall of the tube by the pressure must be overcome. Thus, in practice, a significant pinching force is required regardless of whether a tube is connected to a vacuum source or a source of pressurized fluid.

Another embodiment disclosed in the '551 patent uses a mechanical pinching mechanism mounted in the endoscope handle that selectively pinches a resilient tube extending through the handle. The pinching mechanism employs a mechanical advantage between a manually controlled actuating member and a pinching member that is coupled to the actuating member. This mechanic advantage overcomes the significant force required to pinch the tube. However, because of the mechanical advantage used to generate the necessary pinching force, a fairly large movement of the actuating member is required. This large required movement of the actuating member can make it difficult to adequately manipulate the actuating member during an endoscopic procedure.

An unsupported tube that meets the requirements of the valve systems disclosed in the '551 patent is very stiff and requires significant pinching force to close. This high pinching force is of little concern when the pinch valve is located in a remotely activated control box or is acted upon with a significant mechanical advantage. However, when the pinch valve is mounted in or on the control body of the endoscope and it is pinched without any significant mechanical advantage, actuation of the pinch valve would require a sufficient force to cause an endoscopist to become very fatigued because of the frequent actuation of such a valve during an endoscope procedure.

SUMMARY OF THE INVENTION

The present invention provides a pressure equalized flow controller that controls the flow of fluid through a resilient tube. The flow controller includes an enclosed chamber through which a hollow resilient fluid conduit extends between inlet and outlet ports. A pressure equalizing vent couples the interior of the fluid conduit with the interior of the chamber surrounding the fluid conduit to equalize the fluid pressure between the interior and the exterior of the fluid conduit within the chamber. Preferably the pressure equalizing vent is an aperture extending through a wall of the fluid conduit within the chamber. By equalizing the pressure, the flexible tube can have a relatively thin wall without collapsing the tube when high negative fluid pressure is applied to the resilient tube and high positive pressure does not exert an outward force on the wall of the tube.

In a preferred embodiment, the flow controller is a pressure equalized valve that includes a valve actuator structured and positioned to exert sufficient pressure on the flexible tube portion to deform the flexible tube portion and thereby restrict fluid flow through the fluid conduit when the fluid within the fluid conduit is at a first fluid pressure level. The relatively thin wall made possible by the pressure equalizing vent enables the valve actuation to be very easy without the need for any mechanical advantage or electrical actuation devices required to close prior art thick tubes. The valve can be a normally open valve in which the valve actuator includes a spring member biased toward a position in which the spring member exerts insufficient pressure on the flexible tube to restrict fluid flow. The spring member is then moved to a position where it pinches the tube by manually pressing on an actuator member that extends into the chamber and is mechanically coupled to the spring member. Alternatively, the valve can be a normally closed valve in which a spring member is resiliently biased toward a position in which the spring member exerts sufficient pressure on the flexible tube portion to restrict fluid flow. In this alternative valve actuator, the pressing on the actuator member moves the spring member to a position where it no longer pinches the tube.

The valve of the present invention can be self-actuated using a positive or negative pressure differential, and thereby act as a pressure or suction relief valve. To act as a suction relief valve, the actuating member has a cross-sectional area outside of the valve chamber sufficient to enable a predetermined negative pressure differential between the inside and the outside of the valve chamber to move the actuating member, thereby opening the valve. To act as a positive pressure relief valve, the actuating member preferably has a cross-sectional area inside of the valve chamber sufficient to enable a predetermined positive pressure differential between the inside and the outside of the valve chamber to move the actuating member thereby opening the valve.

DETAILED DESCRIPTION OF THE INVENTION

The present invention is directed to a pressure equalized flow control apparatus and method that control the flow of fluid through a resilient tube. The invention surrounds the resilient tube in an enclosed chamber having inlet and outlet ports in fluid communication with the interior of the resilient tube. A vent connecting the interior of the resilient tube with the interior of the enclosed chamber enables the fluid pressure inside the resilient tube to equalize with the fluid pressure outside the resilient tube within the enclosed chamber. By equalizing the pressures inside and outside of the resilient tube, the invention prevents the resilient tube from collapsing when the resilient tube is under suction. Similarly, the pressure equalization prevents a positive pressure from exerting an outward force on the wall of the time which could rupture the tube and/or make it more difficult to collapse the tube. Thus, by using pressure equalization, the invention enables the resilient tube to have a relatively thin wall. Such a relatively thin wall enables a simple pinch valve to easily pinch the resilient tube closed without using the electrical or mechanical advantage devices of prior art pinch valves.

Figure 1:
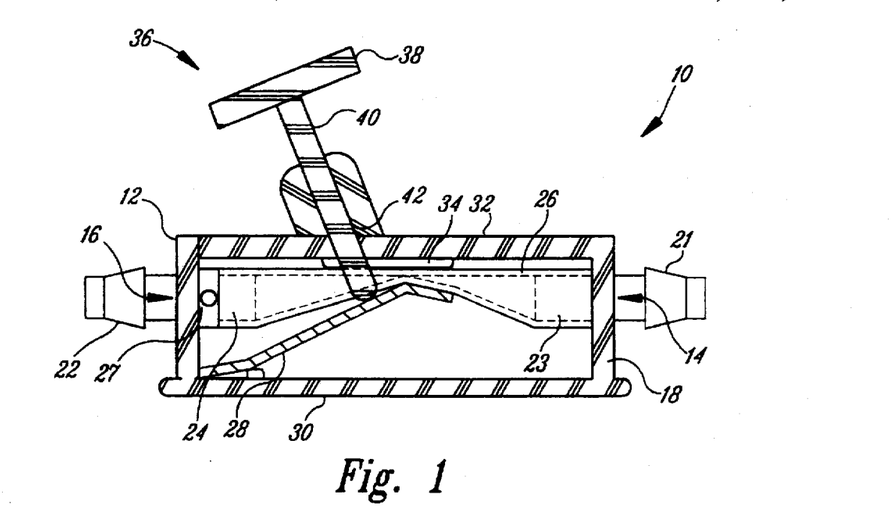
FIG. 1 is a side cross-sectional view of a normally closed valve in a closed position according to the present invention.

As shown in FIG. 1, the flow control apparatus of the present invention is embodied in a pressure-equalized valve 10. The valve 10 includes an enclosed chamber 12 having an inlet port 14 and an outlet port 16 extending through first and second end walls 18, 20, respectively. The designation of the inlet and outlet ports 14, 16 is arbitrary in that fluid can flow in either direction through each of the ports. Extending outwardly from the inlet and outlet ports 14, 16 are an external inlet nozzle 21 and an external outlet nozzle 22 for connecting the valve 10 to tubes (FIG. 8) carrying the fluid to and from the valve. For example, the external inlet nozzle 21 can be coupled to the suction tube of an endoscope (FIG. 8) and the external outlet nozzle 22 can be coupled to the suction source.

Figure 2:
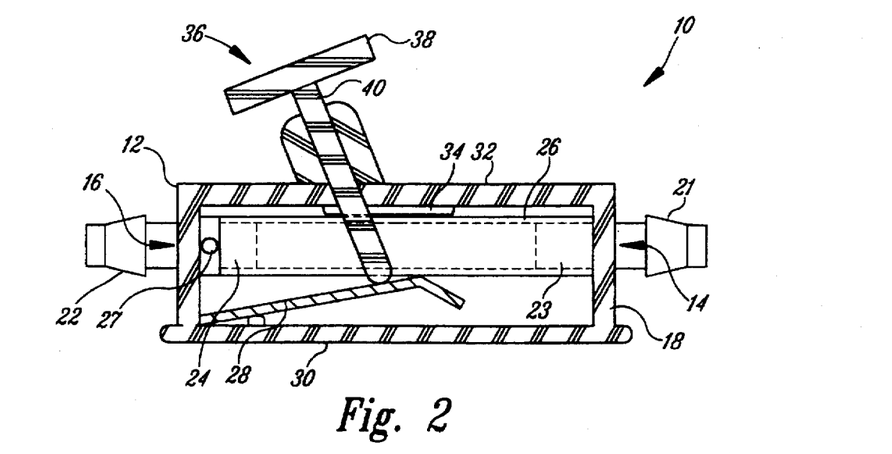
FIG. 2 is a side cross-sectional view of the normally closed valve of FIG. 1 in an open position.

As shown in FIG. 1, extending into the enclosed chamber 12 from the inlet port 14 and the outlet port 16 are an internal inlet nozzle 23 and an internal outlet nozzle 24, respectively. A resilient tube 26 is coupled between the internal inlet nozzle 23 and the internal outlet nozzle 24 such as by coaxially fitting opposite ends of the flexible tube on the respective internal nozzles. The resilient tube 26 can be made of any resilient material, such as plastic or rubber, and in the preferred embodiment the material used is urethane with embedded oil (C-flex). The internal inlet and outlet nozzles 23, 24 and the flexible tube 26 together comprise a valve conduit in communication with the inlet and outlet ports 14, 16 to enable fluid to flow from the inlet port 14 to the outlet port 16 when the resilient tube 26 is in an open position (FIG. 2).

In order to equalize the fluid pressure between the inside and the outside of the resilient tube 26 within the enclosed chamber 12, a pressure equalizing vent 27 extends through the internal outlet nozzle 24. When fluid flows through the resilient tube 26, a portion of the fluid flows through the vent 27 into the enclosed chamber 12, thereby equalizing the fluid pressures on the inside and outside of the resilient tube. Such pressure equalization prevents a high negative or positive fluid pressure from exerting an inward or outward force, respectively, on the wall of the resilient tube 26. As a result, the resilient tube 26 can have a relatively thin wall (e.g., 0.01 inches).

The valve 10 shown in FIG. 1 is a pinch valve that employs a spring clamp 28 to pinch the resilient tube 26 and thereby restrict fluid flow through the tube 26. The spring claim 28 is affixed to a bottom wall 30 and extends toward a top wall 32 of the enclosed chamber 12. The spring clamp 28 is biased toward the resilient tube 26 such that the spring clamp 28 exerts sufficient pressure to pinch the resilient tube 26 and thereby restrict fluid flow through the tube 26 in the absence of any countervailing force against the spring clamp 28. Preferably, a valve seat 34 extends toward the spring clamp 28 such that the resilient tube 26 is pinched between the spring clamp 28 and the valve seat 34 when the valve 10 is closed. A valve actuator 36 includes an actuation button 38 and a valve stem 40 that extends through an aperture 42 in the top wall 32 of the enclosed chamber 12. To open the valve 10, a user can press the actuation button 38 which causes the valve stem 40 to move farther into the enclosed chamber 12 and push the spring clamp 28 away from the valve seat 32, thereby enabling fluid to flow through the resilient tube 26 as shown in FIG. 2.

Given the relatively thin wall of the resilient tube 26 resulting from the pressure equalization provided by the vent 27, the spring clamp 28 can be a relatively weak spring (e.g., 30 grams of spring force) and still pinch the resilient tube 26 sufficiently to prevent fluid flow through the tube. Using such a low strength spring clamp 28, a user can easily depress the actuation button 38 of the valve actuator 36 to cause the valve stem 40 to release the spring claim 28 and thereby open the resilient tube 26. Moreover, since the valve stem 40 acts directly against the spring clamp 28 without any intervening mechanical advantage, the stroke of the valve stem between its open and closed positions can be relatively short. If such a thin-walled resilient tube 26 were used in prior art pinch valves, the resilient tube would collapse when more than a small amount of suction was applied to the resilient tube. However, the vent 27 prevents such a thin-walled tube 26 from collapsing by equalizing the fluid pressure inside and outside the resilient tube 26.

Although one skilled in the art could easily design the resilient tube 26 and the pressure equalizing vent 27 with various dimensions and configurations, a preferred embodiment of the invention employs a resilient tube with an internal diameter of 0.1 inches and a pressure equalizing vent with a diameter of 0.05 inches. In addition, the wall thickness in the preferred embodiment is 0.01 inches which contrasts with the approximately 0.06 wall thickness typical of the thick-walled tubes used in prior art pinch valves. Moreover, the vent 27 could extend through the flexible tube 26 or the inlet interior nozzle 22 rather than the outlet interior nozzle 24.

Figure 3:
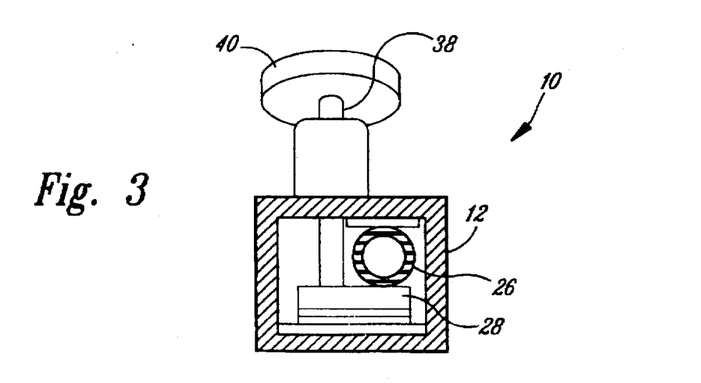
FIG. 3 is a from cross-sectional view of the valve shown in FIG. 1 in the open position.

Shown in FIGS. 2 and 3 is the same valve 10 shown in FIG. 1, but the valve stem 40 has been actuated to depress the spring clamp 28 and thereby open the valve. One method of actuating the valve stem 40 to open the valve is by a user manually pressing the actuation button 38 of the valve actuator 36. Alternatively, the valve stem 40 can be actuated automatically by taking advantage of a pressure differential in the enclosed chamber 12 with respect to the area outside of the enclosed chamber. In particular, when a suction is applied to the fluid in the resilient tube 26, the fluid flows through the vent 27 and thereby reduces the pressure in the enclosed chamber 12 below that of the ambient pressure surrounding the outside of the enclosed chamber 12. If the suction is sufficiently strong, the pressure differential will be sufficient to push the valve stem 40 into the enclosed chamber and thereby depress the spring clamp 28 and open the resilient tube 26. In this situation, the valve 10 acts as a suction relief valve that automatically opens when a predetermined suction level has been reached. Those skilled in the art can appropriately size the diameter of the valve actuator 36 to provide the automatic actuation, which would also depend on the strength of the spring clamp 28 and the friction of the valve stem 38 with respect to the top wall 32 of the enclosed chamber 12.

Figure 4:
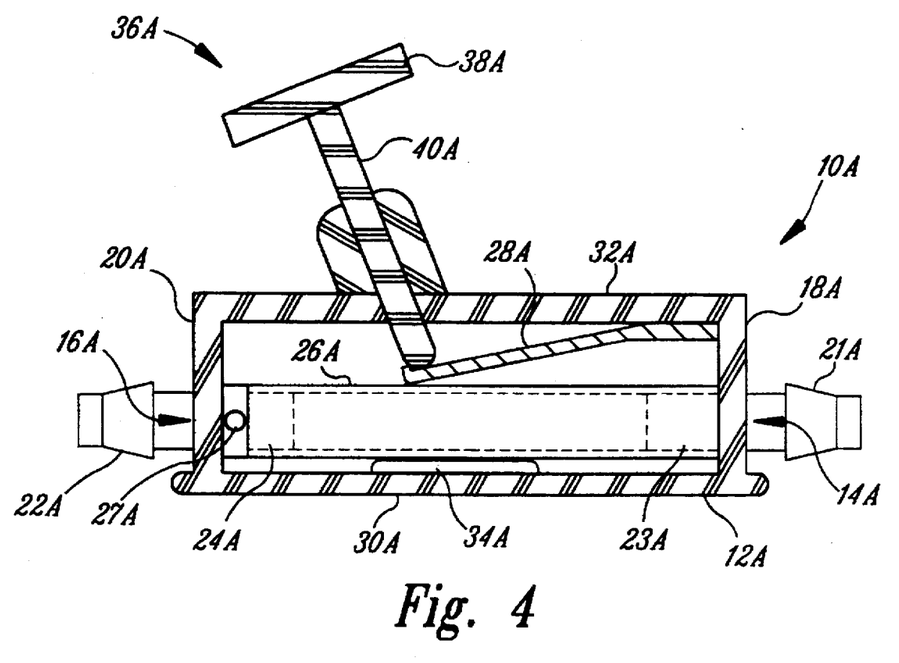
FIG. 4 is a side cross-sectional view of a normally open valve in an open position according to the present invention.

As shown in FIG. 4, the flow control apparatus of the present invention can be embodied in an alternate valve 10A, which is a normally open valve. Each of the elements of the valve 10A shown in FIG. 4 correspond to analogous elements of the normally closed valve 10 shown in FIG. 1 and thus are numbered similarly with the addition of the letter A. The elements of the valve 10A are discussed only to the extent that they differ from the elements of the valve 10 shown in FIG. 1. The primary difference between the normally open valve 10A of FIG. 4 and the normally closed valve 10 of FIG. 1 is that the spring clamp 28A is biased away from the resilient tube 26A. As a result, the spring clamp 28A does not pinch the resilient tube 26A and the resilient tube 26 remains open without the valve actuator 36 being actuated.

Figure 5:
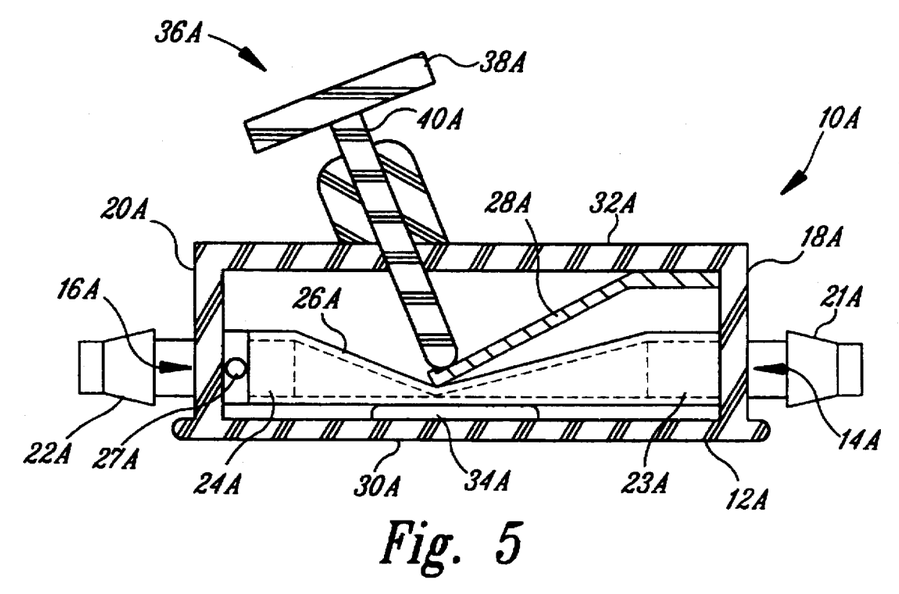
FIG. 5 is a side cross-sectional view of the normally open valve of FIG. 4 in a closed position.

Shown in FIG. 5 is the same normally open valve 10A shown in FIG. 4, but the valve actuator 36A has been actuated to depress the spring clamp 28A into the resilient tube 26A. When the valve actuator 36A is actuated sufficiently, the spring clamp 28A pinches the resilient tube 26A against the valve seat 32A and thereby closes the resilient tube, as shown in FIG. 5. The valve actuator 36A is actuated manually by a user when the user desires to shut off fluid flow in the resilient tube 26A.

Figure 6:
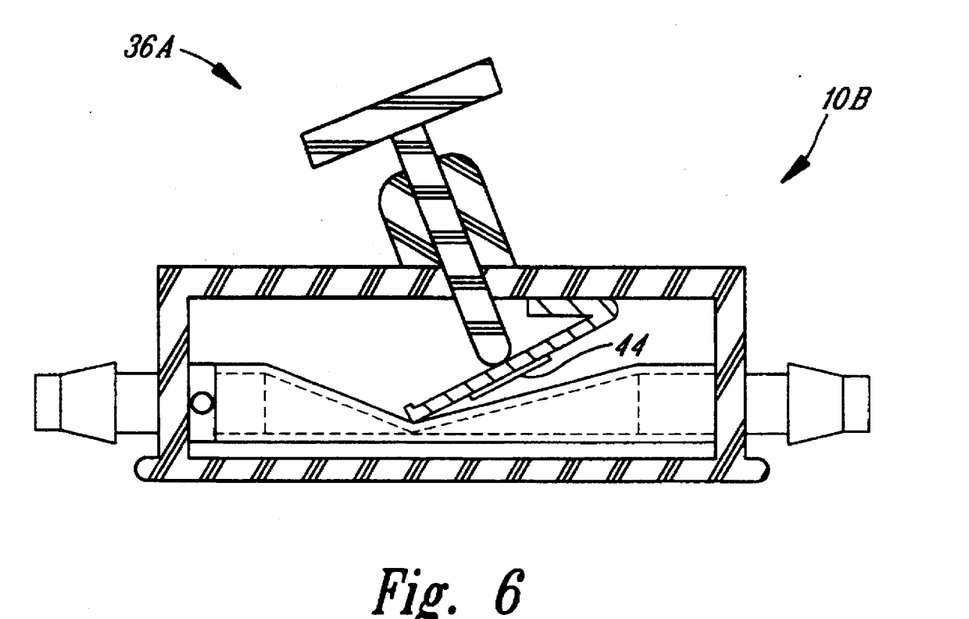
FIG. 6 is a side cross-sectional view of an alternate, normally closed valve according to the present invention.

Shown in FIG. 6 is an alternate embodiment of a normally closed flow control valve 10B. Again, the elements of the valve 10B shown in FIG. 6 are essentially the same as used in the normally closed valve 10 shown in FIG. 1, and thus are numbered similarly with the addition of the letter B. The elements of the valve 10B are discussed only to the extent that they differ from the elements of the valve 10 shown in FIG. 1.

Like the spring clamp 28 shown in FIG. 1, the spring clamp 28B is biased toward the spring seat 34B in order to pinch the resilient tube 26B closed and thereby restrict fluid flow through the resilient tube. However, unlike the embodiment shown in FIG. 1, the spring clamp 28B is connected to the top wall 32B and the spring seat 34B extends from the bottom wall 30B. In addition, the valve stem 40B extends through the spring clamp 28B and ends in a valve stem flange 44 on the opposite side of the spring clamp 28B from the actuation button 38B. The valve 10B can be actuated manually by a user pulling the valve actuator 36B outwardly from the enclosed chamber to open the valve.

An advantage of the flow control valve 10B shown in FIG. 6 is that the valve can be used as a positive pressure relief valve. To open the valve 10B, the valve actuator 36B can be actuated automatically by taking advantage of a positive pressure differential between the inside and the outside of the enclosed chamber 12. In particular, when positive pressure is applied to the fluid in a resilient tube 26B, a portion of the fluid flows through the vent 27B and thereby increases the pressure in the enclosed chamber 12 above that of the ambient pressure surrounding the outside of the enclosed chamber. If the pressure applied is sufficiently strong, the pressure differential will be sufficient to push the valve stem 40B outwardly from the enclosed chamber 12 and thereby pull the spring clamp 28B away from the resilient tube 26B to open the valve 10B. As a result, the valve 10B operates as a pressure relief valve that automatically opens when a predetermined pressure level has been reached. Those skilled in the art can appropriately size the valve stem 40 to provide the automatic actuation.

An advantage of the valves 10, 10A, and 10B is that the valve actuators 36, 36A, 36B, are very simple designs that can be made inexpensively enough to be disposable.

However, it should be appreciated that numerous other types of valve actuators could be employed to open or close the valve. For example, the valve actuators shown in U.S. Pat. No. 4,852,551, which is incorporated herein by reference, could be employed together with a pressure equalizing vent according to the present invention.

Figure 7:
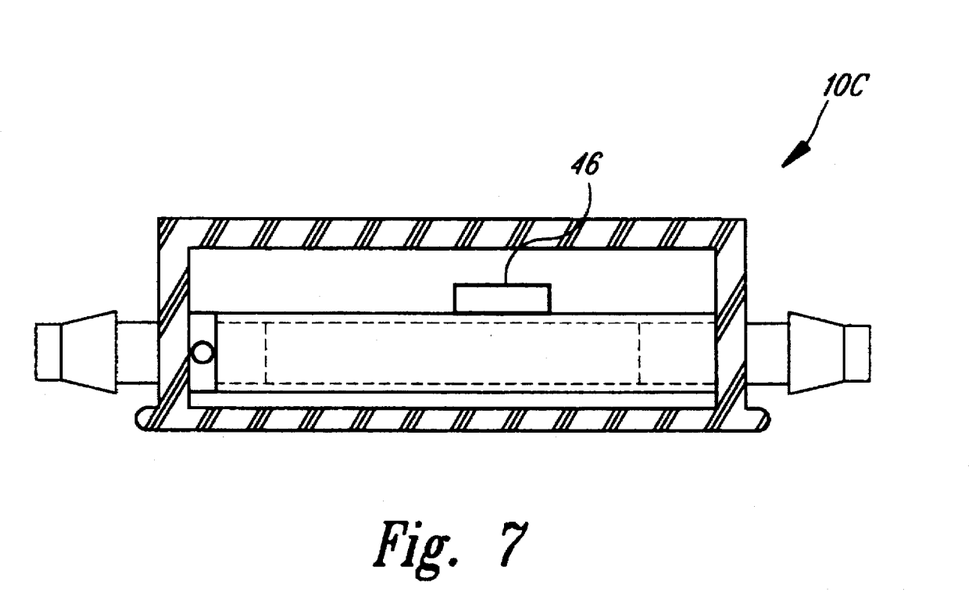
FIG. 7 is a side cross-sectional view of a flow control apparatus according to the present invention.

Another alternate embodiment of the invention is the flow control apparatus 10C shown in FIG. 7. The flow control apparatus 10C is similar to the valves 10, 10A, 10B, shown in FIGS. 1-6 except that the flow control apparatus 10C has no valve actuator. Instead, conventional flow sensor 46 is coupled to the flexible tube 26C in order to monitor the flow of fluid through the flexible tube. For example, the fluid sensor 46 can be an ultrasonic sensor that uses ultrasonic waves to measure the flow of fluid through the flexible tube. The pressure equalization provided by the vent 27C controls the flow through the flexible tube 26C by preventing the flexible tube from collapsing or rupturing. Such an ultrasonic sensor benefits from being used with the thin-walled resilient tube 26C that is rendered possible by the pressure equalization afforded by the present invention.

Figure 8:
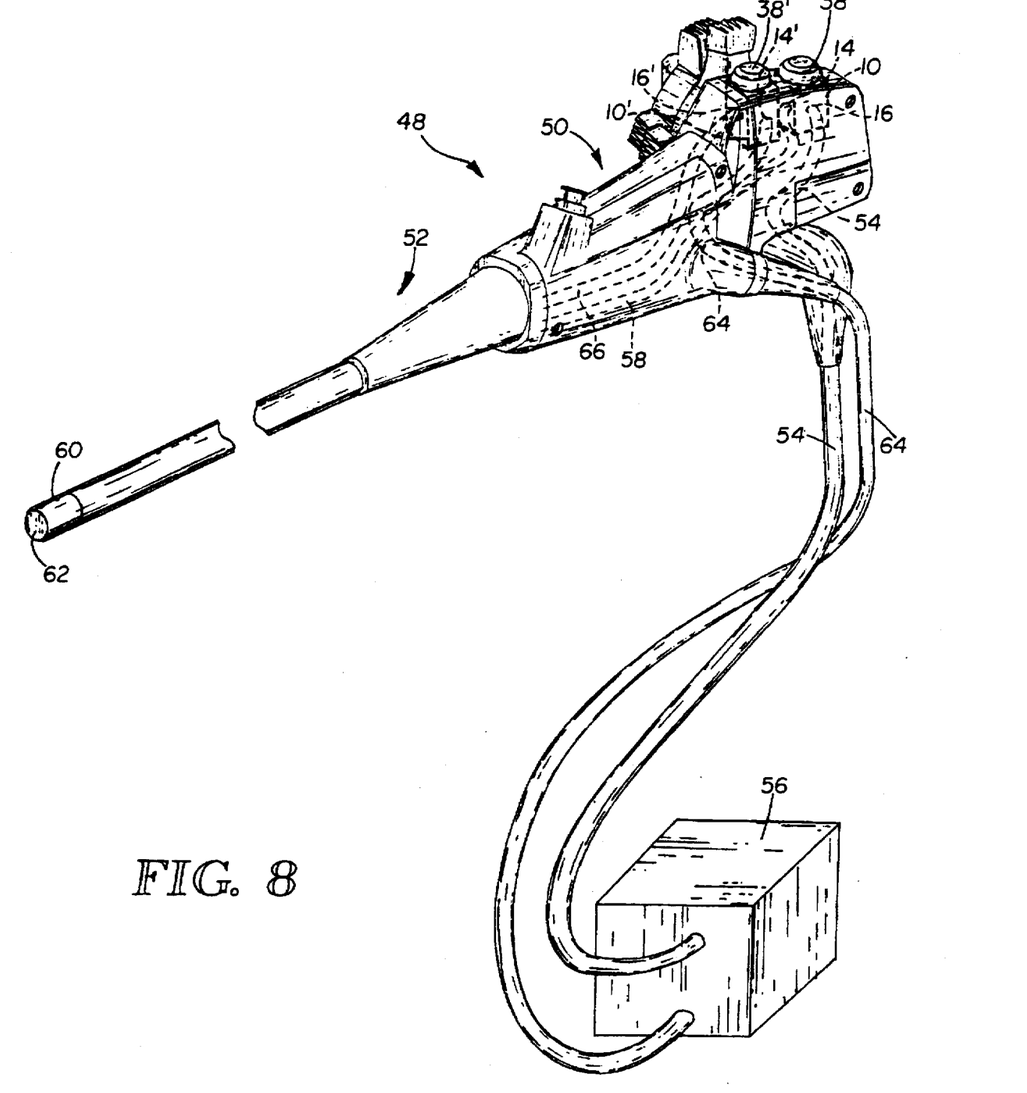
FIG. 8 is an isometric view of an endoscope including valves according to the present invention.

One particularly important application employing any one of the valves 10, 10A, 10B shown in FIGS. 1-6 is in conjunction with an endoscope. Shown if FIG. 8 is an endoscope 48 having a control handle 50 and an elongated insertion tube 52 extending from the control handle. A suction valve 10 and a water valve 10' designed as shown in FIGS. 1-3 are coupled to and positioned partially within the control handle 50. The suction valve 10 is connected at its output port 16 to a suction source tube 54 extending from an external fluid/suction source 56. An endoscope suction tube 58 extends from the inlet port 14 of the suction valve 10 through the control handle 50 to a distal end 60 of the endoscope insertion tube 52. The fluid/suction source 56 produces a suction in the suction source tube 54, but no suction is produced in the endoscope suction tube 58 when the suction valve 10 is in a closed position as shown in FIG. 1. However, when a user presses the valve actuation button 38, the valve stem 40 opens the resilient tube 26 in the suction valve 10 (FIG. 2) thereby enabling fluid to flow by suction from the distal end 60 of the insertion tube 52 to the fluid/suction source 56, through the suction tube 58, suction valve 10, and the suction source tube 54. As discussed above, the pressure equilization provided by the pressure equilizing vent 27 enables the resilient tube 26 to be thin-walled which only requires a light actuation force on the valve actuation button 38 to open the valve 10 in order for the endoscope 48 to suction fluids out of a patient's body.

The irrigation valve 10' in the endoscope control handle 50 shown in FIG. 8 regulates the flow of water or other fluid to the distal end 60 of the insertion tube 52. Typically, such water is directed towards a lens 62 at the distal end 60 of the insertion tube 52 in order to clean off mucus, stool, or blood from the lens, which would otherwise obscure the view through the lens. To provide such controllable water flow, the irrigation 10' is connected at its inlet port 14' to a water source tube 64 extending from the fluid/suction supply 56 and is connected at its outlet port 16' to an irrigation tube 66 extending from the distal end 60 of the endoscope insertion tube 52. When the irrigation valve 10' is in a closed position as shown in FIG. 1, the irrigation valve prevents water from flowing from the fluid/suction supply 56 to the irrigation tube 66. However, when a user presses the actuation button 38' the irrigation valve 10' is opened as shown in FIG. 2 and the water flows from the fluid/suction supply 56 to the distal end 60 of the insertion tube 52 through the water supply tube 64, the irrigation valve 10', and the irrigation tube 66. As discussed above, the actuation force needed to actuate the valve actuation button 38' and thereby open the irrigation valve 10' is relatively small because of the pressure equilization provided by the pressure equilizing vent 27'.

As will be appreciated based on the foregoing discussion, the present invention provide a simple and inexpensive flow control apparatus and method for controlling the flow of fluid through a resilient tube. The pressure equalization techniques of the present invention enable the resilient tube to have a very thin wall which provides numerous advantages. Such a thin-walled resilient tube allows a very simple valve actuator to be used to open or close the flexible tube. Such a simple valve design is inexpensive enough to be disposable when used in procedures, such as endoscopic procedures, in which the valve can become contaminated. The disposability of the valve enables the valve to be used in an endoscope without having to clean the valve between uses of the endoscope. The time saved by not having to clean the valve enables many more endoscopic procedures to be performed, thereby decreasing the cost per procedure of the endoscope.

It will be appreciated that, although specific embodiments of the invention have been described herein for purposes of illustration, various modifications may be made without departing from the spirit and scope of the invention. Accordingly, the invention is not limited except as by the appended claims.

I claim:

1. A pressure equalized valve, comprising:

an enclosed valve chamber having inlet and outlet ports allowing passage of fluid into and out of the valve chamber;

a hollow valve conduit positioned within the valve chamber and connecting the inlet port with the outlet port, the valve conduit including a resilient tube with an interior and an exterior;

a valve actuator positioned at least partially within the valve chamber, the valve actuator being configured to control pinching and unpinching of the resilient tube to regulate fluid flow through the resilient tube of the valve conduit; and a pressure equalizing vent coupling the interior of the valve conduit with the exterior of the valve conduit within the valve chamber in a manner that ensures that a fluid pressure within the valve conduit substantially equals a fluid pressure on the exterior of the valve conduit within the valve chamber.

2. The pressure equalized valve of claim 1 wherein the pressure equalizing vent is an aperture extending through a wall of the valve conduit within the valve chamber.

3. The pressure equalized valve of claim 1 wherein the valve actuator is structured and positioned to exert sufficient pressure on the resilient tube to deform the resilient tube and thereby restrict fluid flow through the fluid conduit when the fluid within the fluid conduit is at a first fluid pressure level.

4. The pressure equalized valve of claim 3 wherein the valve actuator includes a spring member biased toward a position in which the spring member does not exert pressure on the resilient tube sufficient to restrict fluid flow through the resilient tube.

5. The pressure equalized valve of claim 3 wherein the valve actuator includes a spring member biased toward a position in which the spring member exerts sufficient pressure on the resilient tube to restrict fluid flow through the resilient tube.

6. The pressure equalized valve of claim 5 wherein the valve actuator further includes a valve stem extending through a wall of the valve chamber and contacting the spring member, the valve stem having a cross-sectional area extending into the valve chamber sufficient to enable a predetermined negative pressure differential occurring in the valve chamber with respect to the outside of the valve chamber to cause the valve stem to move into the valve chamber and against the spring member, and thereby reduce the pressure exerted on the resilient tube by the spring member, the negative pressure differential being caused by suction of fluid out of the valve chamber.

7. The pressure equalized valve of claim 5 wherein the valve actuator further includes a valve stem extending through a wall of the valve chamber and contacting the spring member, the valve stem having a cross-sectional area extending into the valve chamber sufficient to enable a predetermined positive pressure differential occurring in the valve chamber with respect to the outside of the valve chamber to cause the valve stem to move outwardly from the valve chamber and against the spring member, and thereby reduce the pressure exerted on the resilient tube by the spring member, the pressure differential being caused by forced fluid flow into the valve chamber.

8. The pressure equalized valve of claim 1, further comprising:

an endoscope having a control handle and an elongated insertion tube extending from the control handle, the valve chamber being coupled to the control handle, the endoscope also including a fluid tube extending from the outlet port of the valve chamber to a distal end of the insertion tube, the valve actuator regulating fluid flow through the fluid tube by regulating the fluid flow through the resilient tube within the valve chamber.

9. A pressure equalized apparatus for providing controllable fluid flow, comprising:

an enclosed chamber having inlet and outlet ports allowing passage of fluid into and out of the chamber;

a hollow fluid conduit being positioned within the chamber and connecting the inlet port with the outlet port, the fluid conduit including a resilient tube and having an interior; and a pressure equalizing vent coupling the interior of the fluid conduit with the chamber outside the fluid conduit in a manner that ensures that a fluid pressure within the fluid conduit substantially equals a fluid pressure on the exterior of the fluid conduit within the chamber.

10. The pressure equalized apparatus of claim 9 wherein the pressure equalizing vent is an aperture extending through a wall of the fluid conduit within the chamber.

11. The pressure equalized apparatus of claim 9, further comprising:

a valve actuator structured and positioned to exert sufficient pressure on the resilient tube to deform the resilient tube and thereby restrict fluid flow through the fluid conduit when the fluid within the fluid conduit is at a first fluid pressure level.

12. The pressure equalized apparatus of claim 11 wherein the valve actuator includes a spring member biased toward a position in which the spring member does not exert pressure on the resilient tube sufficient to restrict fluid flow through the resilient tube.

13. The pressure equalized apparatus of claim 11, further comprising:

an endoscope having a control handle and an elongated insertion tube extending from the control handle, the enclosed chamber being coupled to the control handle, the endoscope also including a fluid tube extending from the outlet port of the enclosed chamber to a distal end of the insertion tube, the valve actuator regulating fluid flow through the fluid tube by regulating the fluid flow through the resilient tube within the enclosed chamber.

14. The pressure equalized apparatus of claim 11 wherein the valve actuator includes a spring member biased toward a position in which the spring member exerts sufficient pressure on the resilient tube to restrict fluid flow through the resilient tube.

15. The pressure equalized apparatus of claim 14 wherein the valve actuator further includes a valve stem extending through a wall of the valve chamber and contacting the spring member, the valve stem having a cross-sectional area extending into the valve chamber sufficient to enable a predetermined negative pressure differential occurring in the valve chamber with respect to the outside of the valve chamber to cause the valve stem to move into the valve chamber and against the spring member, and thereby reduce the pressure exerted on the resilient tube by the spring member, the negative pressure differential being caused by suction of fluid out of the valve chamber.

16. The pressure equalized apparatus of claim 14 wherein the valve actuator further includes a valve stem extending through a wall of the valve chamber and contacting the spring member, the valve stem having a cross-sectional area extending into the valve chamber sufficient to enable a predetermined positive pressure differential occurring in the valve chamber with respect to the outside of the valve chamber to cause the valve stem to move outwardly from the valve chamber and against the spring member, and thereby reduce the pressure exerted on the resilient tube by the spring member, the pressure differential being caused by forced fluid flow into the valve chamber.

17. A method of allowing controllable fluid flow through a resilient tube having an interior an an exterior, comprising:
providing an enclosed chamber surrounding at least a portion of the resilient tube, the enclosed chamber having inlet and outlet ports in fluid communication with the interior of the resilient tube;
equalizing fluid pressure on the exterior of the resilient tube within the enclosed chamber with fluid pressure within the resilient tube by venting the interior of the resilient tube to the enclosed chamber.

18. The method of claim 17 wherein the equalizing step includes venting fluid from the interior of the resilient tube to the exterior of the resilient tube within the enclosed chamber.

19. The method of claim 17 wherein the equalizing step includes venting fluid from the exterior of the resilient tube within the enclosed chamber to the interior of the resilient tube.

20. The method of claim 17, further comprising:
exerting sufficient pressure on the exterior of the resilient tube to deform the resilient tube and thereby restrict the fluid flow through the resilient tube.

21. The method of claim 20, further comprising:
providing a valve actuator extending from a wall of the enclosed chamber, the valve actuator performing the exerting step.

22. The method of claim 21, further comprising:
providing fluid flow within the resilient tube sufficient to overcome the pressure exerted on the exterior of the resilient tube by the valve actuator, and thereby enabling increased fluid flow through the resilient tube.

23. The method of claim 21 wherein the valve actuator extends through the wall of the enclosed chamber, the method further comprising:
providing a pressure differential within the enclosed chamber with respect to an area outside the enclosed chamber, the pressure differential being sufficient to overcome the pressure exerted on the exterior of the resilient tube by the valve actuator, and thereby enabling increased fluid flow through the resilient tube.

24. The method of claim 23 wherein the step of providing a pressure differential includes venting fluid from the interior of the resilient tube to the exterior of the resilient tube within the enclosed chamber, such that the pressure differential is positive in the enclosed chamber with respect to the area outside the enclosed chamber.

25. The method of claim 23 wherein the step of providing a pressure differential includes venting fluid from the exterior of the resilient tube within the enclosed chamber to the interior of the resilient tube, such that the pressure differential is negative in the enclosed chamber with respect to the area outside the enclosed chamber.

* * * * *

UNITED STATES PATENT AND TRADEMARK OFFICE
CERTIFICATE OF CORRECTION

PATENT NO.    :   5,692,729
DATED         :   December 2, 1997
INVENTOR(S)   :   Edward Paul Harhen It is certified that error appears in the above identified patent and that said Letters Patent is hereby corrected as shown below:

On the cover page under item [75] after "Duxbury," please delete "Miss." and substitute therefor –Mass.--.

In column 11, claim 17, line 36, after "interior" delete "an" and substitute therefor --and--.

Signed and Sealed this

Seventh Day of July, 1998

*Attest:*

*Attesting Officer*

BRUCE LEHMAN

*Commissioner of Patents and Trademarks*